(12) United States Patent
Campo et al.

(10) Patent No.: US 9,462,936 B2
(45) Date of Patent: Oct. 11, 2016

(54) MEDICAL INSTRUMENT, IN PARTICULAR HYSTEROSCOPE

(75) Inventors: Rudi Campo, Genk (BE); Frank Doll, Talheim (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 773 days.

(21) Appl. No.: 12/727,601

(22) Filed: Mar. 19, 2010

(65) Prior Publication Data

US 2010/0268023 A1    Oct. 21, 2010

(30) Foreign Application Priority Data

Mar. 20, 2009   (DE) .................. 10 2009 015 392

(51) Int. Cl.
| | |
|---|---|
| *A61B 1/00* | (2006.01) |
| *A61B 1/303* | (2006.01) |
| *A61B 1/018* | (2006.01) |
| *A61B 1/12* | (2006.01) |
| *A61B 17/42* | (2006.01) |
| *A61B 17/34* | (2006.01) |
| *A61B 17/00* | (2006.01) |

(52) U.S. Cl.
CPC ............. *A61B 1/303* (2013.01); *A61B 1/018* (2013.01); *A61B 1/12* (2013.01); *A61B 17/42* (2013.01); *A61B 17/3494* (2013.01); *A61B 2017/0034* (2013.01); *A61B 2017/3445* (2013.01)

(58) Field of Classification Search
CPC .................................. A61B 1/00154
USPC ........................ 600/105, 121–125
See application file for complete search history.

(56) References Cited

U.S. PATENT DOCUMENTS

| | | | | |
|---|---|---|---|---|
| 3,939,839 | A | * | 2/1976 | Curtiss ........................... 606/46 |
| 4,369,768 | A | * | 1/1983 | Vukovic ....................... 600/123 |
| 4,630,598 | A | * | 12/1986 | Bonnet ......................... 600/135 |
| 4,700,694 | A | * | 10/1987 | Shishido ....................... 600/104 |
| 4,784,117 | A | * | 11/1988 | Miyazaki ....................... 600/114 |
| 4,972,827 | A | * | 11/1990 | Kishi ................. A61B 1/00135 600/114 |
| 5,048,508 | A | | 9/1991 | Storz |
| 5,421,323 | A | * | 6/1995 | Herrmann et al. ........... 600/108 |
| 5,509,892 | A | * | 4/1996 | Bonnet .............. A61B 1/00094 600/129 |
| 5,549,541 | A | * | 8/1996 | Muller .......................... 600/105 |
| 5,630,795 | A | * | 5/1997 | Kuramoto et al. ............. 604/30 |

(Continued)

FOREIGN PATENT DOCUMENTS

| | | |
|---|---|---|
| DE | 3834156 A1 | 4/1990 |
| DE | 3942905 A1 | 6/1991 |

(Continued)

OTHER PUBLICATIONS

European Search Report; Application No. EP 10 15 6953; Jun. 16, 2010; 6 pages.

*Primary Examiner* — Matthew J Kasztejna

(74) *Attorney, Agent, or Firm* — Whitmyer IP Group LLC

(57) ABSTRACT

A medical instrument, in particular a hysteroscope, has a shaft part (12) having a first shaft and an optical system having a second shaft (40), in which the shaft part (12) and optical system can be displaced with respect to one another along the shafts thereof such that, in a first position, the second shaft (40) of the optical system extends beyond the first shaft of the shaft part (12) on the distal side and that, in a second position, a distal end (23) of the first shaft of the shaft part (12) comes to rest approximately level with a distal end (41) of the second shaft (40) of the optical system.

12 Claims, 3 Drawing Sheets

(56) References Cited

U.S. PATENT DOCUMENTS

| | | | |
|---|---|---|---|
| 5,695,448 A * | 12/1997 | Kimura et al. | 600/121 |
| 5,711,756 A * | 1/1998 | Chikama | 600/112 |
| 5,807,237 A * | 9/1998 | Tindel | 600/114 |
| 5,840,013 A * | 11/1998 | Lee et al. | 600/114 |
| 6,471,639 B2 * | 10/2002 | Rudischhauser et al. | 600/128 |
| 7,131,951 B2 * | 11/2006 | Angel | A61B 10/04 600/562 |
| 7,811,228 B2 * | 10/2010 | Adams | 600/121 |
| 7,993,264 B2 * | 8/2011 | Crank | A61B 1/018 600/104 |
| 8,496,574 B2 * | 7/2013 | Trusty | A61B 1/00105 396/17 |
| 9,186,128 B2 * | 11/2015 | Mugan | A61B 10/04 |
| 2005/0228224 A1 * | 10/2005 | Okada et al. | 600/104 |
| 2005/0245875 A1 * | 11/2005 | Restelli | A61M 25/0631 604/164.01 |
| 2005/0288551 A1 * | 12/2005 | Callister et al. | 600/115 |
| 2006/0111613 A1 * | 5/2006 | Boutillette et al. | 600/136 |
| 2006/0189845 A1 * | 8/2006 | Maahs et al. | 600/146 |
| 2007/0238926 A1 * | 10/2007 | Boulais | 600/137 |
| 2008/0262308 A1 * | 10/2008 | Prestezog et al. | 600/123 |
| 2010/0168514 A1 * | 7/2010 | Callister et al. | 600/106 |

FOREIGN PATENT DOCUMENTS

| | | |
|---|---|---|
| DE | 10164384 A1 | 7/2003 |
| DE | 202008010236 U1 | 11/2008 |
| EP | 1152684 B1 | 12/2003 |
| WO | 2008058157 A2 | 5/2008 |
| WO | 2008091995 A2 | 7/2008 |

\* cited by examiner

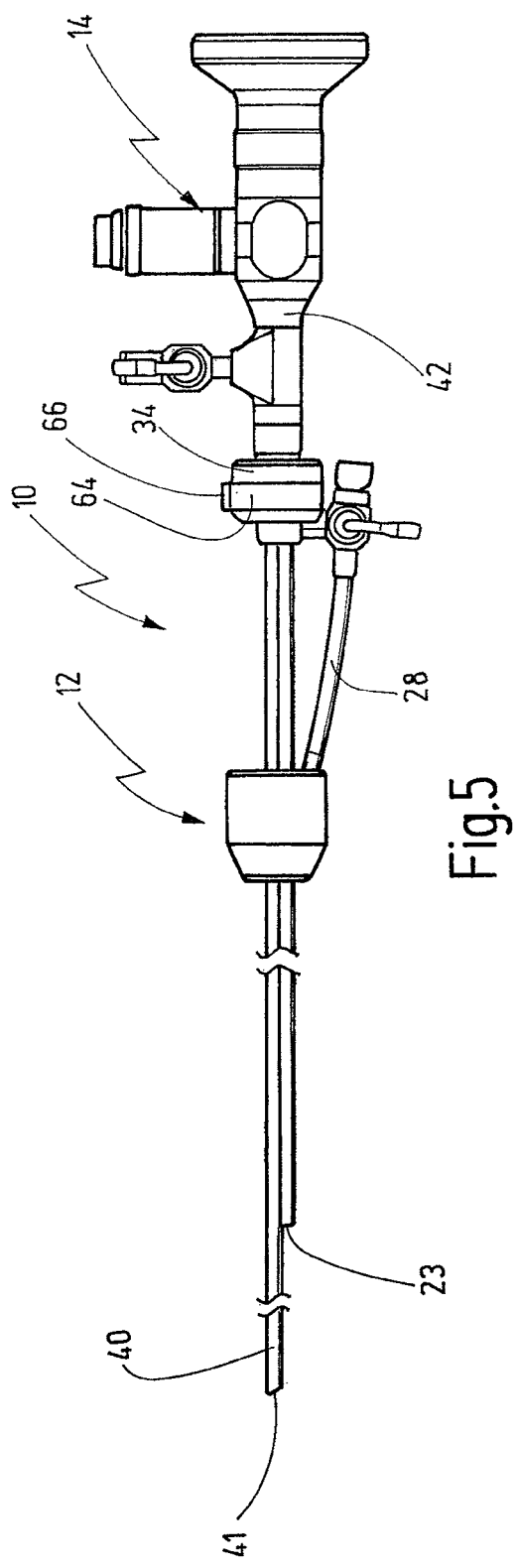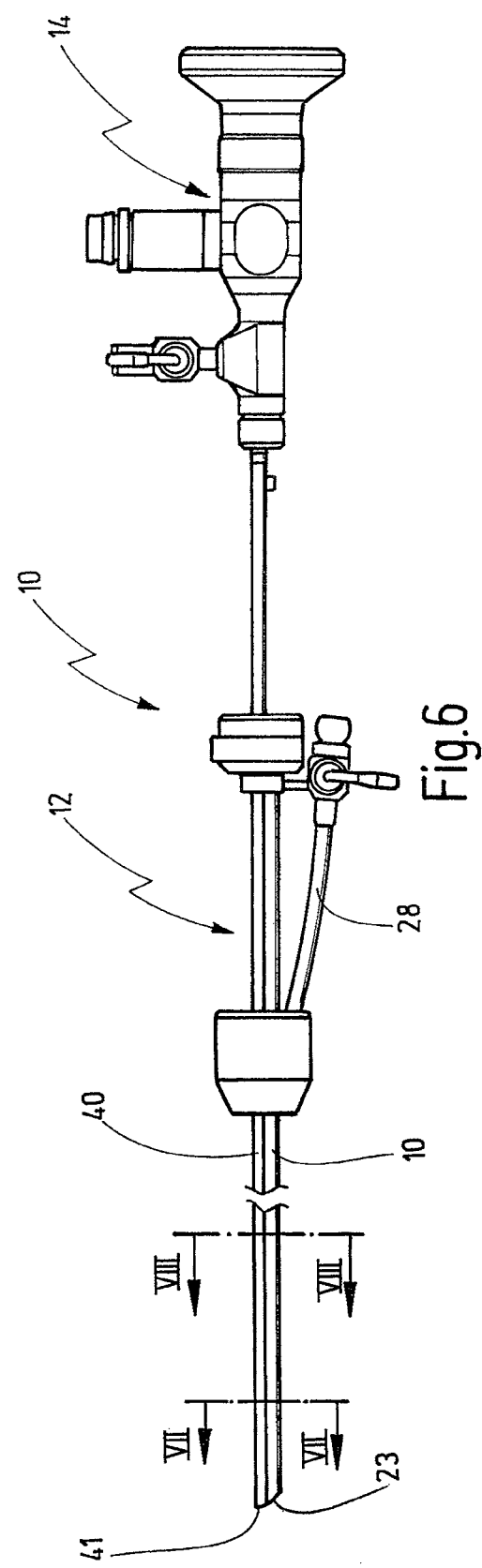

MEDICAL INSTRUMENT, IN PARTICULAR HYSTEROSCOPE

BACKGROUND OF THE INVENTION

The invention relates to an instrument, in particular a hysteroscope.

Hysteroscopes are used for inspecting the uterine cavity or for inserting instruments into the uterus through an endoscope, for example for partial resection of submucous myoma, for laser-surgical separation of septa or for intra-uterine haemostasis.

For this purpose, the catalogue GYN, issue 5, 2008, pages 69/70, of the applicant offers shafts that are used either in examinations or in surgery.

The examination shafts, having a round cross section, are designed as an optical system and are used, for example, for diagnostic purposes, that is to say for the visual inspection of the uterus. To this end, at least the distal end of the shaft is inserted a few centimeters into the uterus through the cervix. This is very painful for the patient, particularly if she has diseases in the region of the uterus.

In order to be able to carry out the examination in an improved fashion, such optical system shafts usually have an irrigation channel as well in order to introduce an irrigation medium into the uterus. At the same time, this irrigation medium is used for dilation, i.e. widening, of the uterus.

If an intervention is intended to be undertaken, the examination shaft is removed and a surgical shaft is inserted, for example a surgical shaft according to BETTOCCHI.

To this end, the examination shaft has to be retracted from the uterus and the surgical shaft subsequently has to be inserted, the latter in turn carrying an optical system and additionally having at least one instrument channel through which it is possible to guide an instrument by means of which the actual intervention in the uterus is carried out.

Thus, for example, should it be discovered during an examination of a uterus by means of an examination shaft that a surgical intervention has to take place immediately, this examination shaft firstly has to be retracted and subsequently the surgical shaft with a significantly larger diameter has to be inserted.

This is not only uncomfortable for the patient but also very painful.

Furthermore, two different instruments have to be provided and kept at the ready.

It is therefore an object of the invention to redress this and to provide a device, in particular a hysteroscope, by means of which both an examination and a surgical intervention can be carried out in the most atraumatic fashion possible.

SUMMARY OF THE INVENTION

This object is achieved by a medical instrument, in particular a hysteroscope, comprising a shaft part having a first shaft, and an optical system having a second shaft, said shaft part and said optical system being mounted in that they are displacable with respect to another along said first and said second shaft, wherein in a first position, said second shaft of said optical system extends beyond a distal end of said first shaft of said shaft part, and in a second position said distal end of said first shaft comes to rest approximately at a level of a distal end of said second shaft.

These measures now have a number of advantages.

In the first position, the instrument, which is assembled from the two components shaft part and optical system, can be used as an examination shaft with a relatively small diameter or cross section because only the second shaft of the optical system protrudes distally in the first position. In this case, for example, the uterus can be examined at first, for which purpose only the second shaft of the optical system has to be inserted.

Should it now transpire that no further manipulations have to be carried out, these two shafts remain in this relative position with respect to one another and the instrument can be retracted from the uterus again after the examination has been carried out.

Should it now transpire that a surgical intervention is necessary, the first shaft of the shaft part is displaced so far distally that it too penetrates the uterus, to be precise so far that the distal end of said first shaft comes to rest approximately level with the distal end of the second shaft of the optical system. The first shaft of the shaft part has now created an instrument channel through which an instrument can be inserted into the uterus in order to carry out an intervention. The second shaft of the optical system already located in the uterus remains there, and this optical system then can be used to observe visually the manipulation within the uterus.

It was determined in practical use that the first shaft of the shaft part, can be introduced into the uterus in a relatively atraumatic fashion along the second shaft of the optical system already inserted into the uterus.

In a refinement of the invention, the cross sections of the two shafts are adjusted with respect to each other such that the two adjoining shafts result in a rounded, approximately oval, overall cross section.

The advantage of this measure is that the two shafts, which are pushed into the uterus and are adjacent to one another, form one body, which can be inserted with as little pain as possible for the patient and which, in the case of manipulations in the uterus, can be moved through the cervix and can be moved to and fro.

In a further refinement of the invention, the first shaft of the shaft part has an instrument channel.

The advantage of this measure is that this first shaft creates the instrument channel for being able to carry out the manipulations in the interior of the uterus by means of the two adjoining shafts. Here, this channel can already exist in advance or only be formed by placing or pushing the two shafts next to one another.

In a further refinement of the invention, the second shaft of the optical system has at least one suction and/or irrigation channel in addition to the optical components.

The advantage of this measure is that, as mentioned previously, this suction and/or irrigation channel can already be used during the examination, for example in order to dilate the uterus. This suction and/or irrigation channel can also be used during the actual surgical intervention in order to supply or discharge irrigation fluids, possibly also to discharge severed tissue parts.

Thus, a very small number of components suffice to be able to carry out the various manipulations, be it an examination or a surgical intervention, with visual monitoring.

In a further refinement of the invention, the first shaft of the shaft part is shaped in a distal end area as an approximately U-shaped shaft that is open on one side, the open side of which can fit closely on the cross-section profile of the second shaft of the optical system.

The significant advantage of this measure is that the first shaft of the shaft part fits closely on the contour of the second shaft of the optical system and so not only is it the case that the aforementioned rounded body is created, but also that the feed motion of the first shaft of the shaft part for inserting and providing the instrument channel can be carried out as atraumatically as possible.

In a further refinement of the invention, on one of the components, that is to say either on the optical system or on the shaft part, there is arranged a guide for guiding the shaft of the other component.

The advantage of this measure is that the guide on the one shaft, should it be necessary, serves to be able to guide the other shaft without problems during a change between said first and said second position and vice versa.

This guiding leads to the two shafts remaining as a tightly-fitted overall body and not running apart in a divergent fashion when seen over a relatively long distance.

In a further refinement of the invention, a latching is provided to latch the two components optical system and shaft part to one another in the two positions.

This has the significant advantage in terms of handling that the operator, if for example only an examination is intended to be carried out, latches the two components to one another in that position, namely in the first position, in which the second shaft of the optical system extends beyond the first shaft of the shaft part on the distal side. If a surgical intervention is to be carried out, the first shaft of the shaft part is displaced that far distally until it reaches the second position, wherein this constitutes the second latching position, i.e. the two shafts or components again latch into one another in this position.

This can be felt by the operator who thus knows that the two shafts now have been brought into the correct position—the correct second position for the intervention.

It is understood that the features mentioned above and yet to be explained below can be used not only in the respectively specified combination, but also in other combinations or on their own, without departing from the scope of the present invention.

BRIEF DESCRIPTION OF THE DRAWINGS

The invention will now be explained and described in more detail on the basis of the subsequent exemplary embodiments in conjunction with the attached figures, in which:

FIG. 5 shows a situation in which the optical system was inserted into the shaft part from proximal to distal such that the two components are in the first position, i.e. the first shaft of the optical system extends beyond the second shaft of the shaft part on the distal side, FIG. 6 shows an illustration corresponding to FIG. 5 in which the two components are in their second position, i.e. the first shaft part was displaced so far distally that the distal ends of the two shafts come to rest approximately level.

DETAILED DESCRIPTION OF PREFERRED EMBODIMENTS

A medical instrument according to the invention, in particular a hysteroscope, illustrated in FIGS. 1 to 8, in particular in FIGS. 5 and 6, is designated in its entirety by the reference sign 10.

Figure 1:
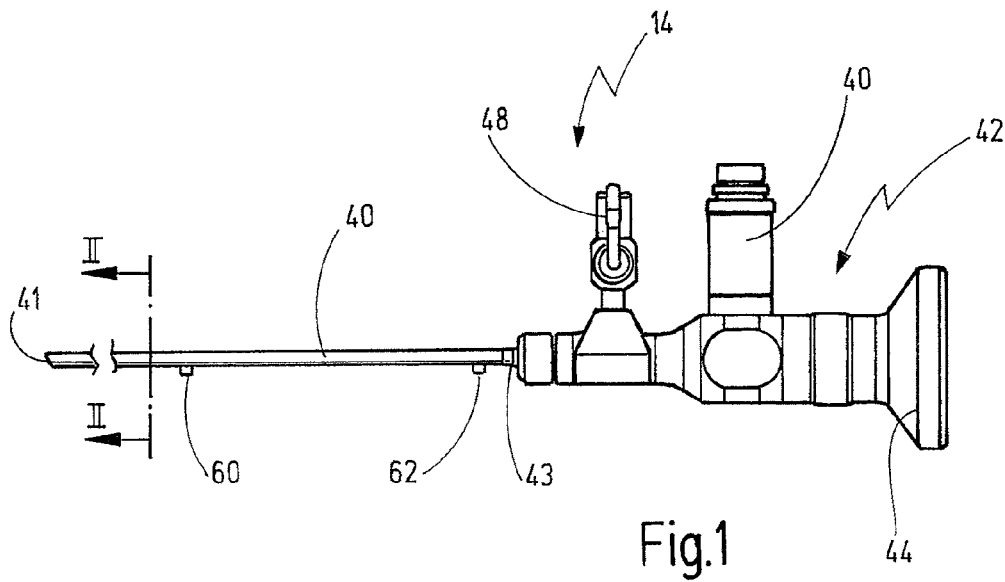
FIG. 1 shows a side view of an optical system.
Figure 3:
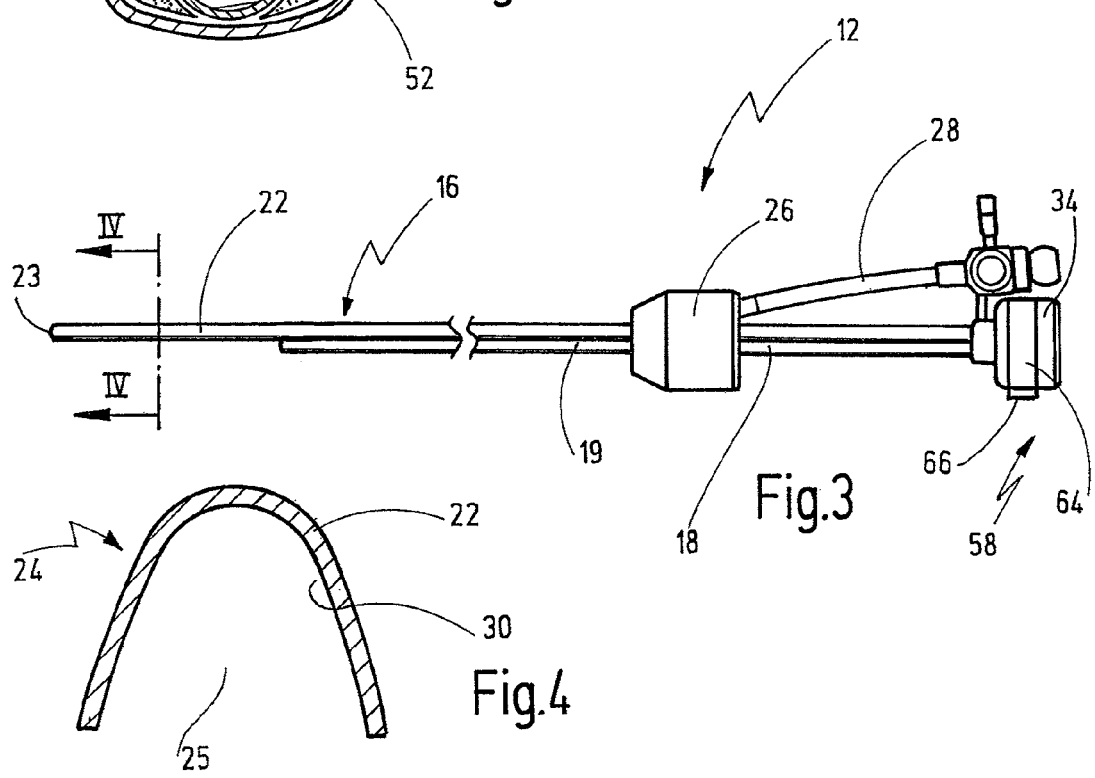
FIG. 3 shows a side view of a shaft part.

The instrument 10, as illustrated in FIGS. 5 and 6, consists of a shaft part 12 illustrated in FIG. 3 and an optical system 14 illustrated in FIG. 1.

The shaft part 12 illustrated in FIG. 3 has a first shaft 16, which has a proximal shaft section 18. The proximal shaft section 18 is a closed shaft and has, as can be seen from the sectional illustration in FIG. 8, an approximately oval cross section 20.

Figure 4:
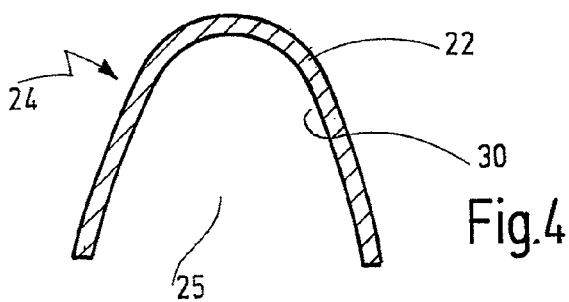
FIG. 4 shows a cross section through the shaft of the shaft part along the line IV-IV in FIG. 3.

On the distal side, the first shaft 16 has a distal shaft section 22, the cross section 24 of which can be seen in FIG. 4. There it can be seen that the cross section 24 of the distal shaft section 22 is approximately U-shaped and open on one side 25.

The distal shaft section 22 ends at a rounded distal end 23.

The first shaft 16 has a housing 26 from which a connection 28 protrudes proximally on the side, which connection can be used to introduce an instrument into the first shaft 16 through the housing 26.

On the proximal side, the first shaft 16 ends in a feeding connector 34, on the outer side of which there is arranged a radially moveable pushbutton 66 of a catch 64.

The optical system 14 illustrated in FIG. 1 has an elongate second shaft 40, which opens into a distal end 41. At its proximal end 43, the second shaft 40 is connected to a housing 42 supporting an eyepiece 44 on the proximal side. Firstly, an optical waveguide connection 46 and, secondly, a suction and irrigation connection 48 with a tap not referred to in any more detail here protrude from the side of the housing 42.

Figure 2:
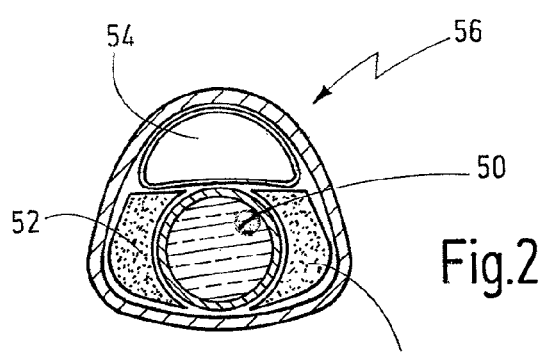
FIG. 2 shows a cross section through the shaft of the optical system along the line II-II in FIG. 1

As can be seen from the sectional illustration of FIG. 2 in particular, there is, in the second shaft 40, an optical system channel 50, in which there are arranged optical waveguides 52 as well in addition to the actual optical elements, i.e. the lenses, as is conventional in an optical system.

Additionally, there is, in the second shaft 40, a suction and irrigation channel 54, which is connected to the suction/irrigation connection 48.

It can be seen from the sectional illustration in FIG. 2 that the second shaft 40 has a cross section 56 that is approximately triangular and provided with two strong and one soft curves.

The side view in FIG. 1 also shows that there are, separated from one another, two latching lugs 60 and 62 of a latching 58 on the outer side of the second shaft 40.

The latching lugs 60 and 62 interact with the above-described catch 64 or the pushbutton 66 on the feeding connector 34 of the first shaft, as will still be explained in more detail below.

FIG. 5 illustrates a situation in which the optical system 14 was pushed through the shaft part 12 from proximal to distal. It should be noted here that, compared to the illustration in FIG. 3, the illustration of the shaft part 12 in FIGS. 5 and 6 is rotated by 180° about the longitudinal axis.

Here, the optical system 14 is inserted so far into the shaft part 12, or, conversely, the shaft part 12 is pushed so far onto the second shaft 40 of the optical system 14, that the feeding connector 34 of the first shaft part 12 comes to rest approximately at the proximal end of the second shaft 40 of the optical system 14 or butts evenly against the housing 42.

This corresponds to the first position between the shaft part 12 and the optical system 14.

In this first position, the latching lug 62 of the optical system 14 (see FIG. 1) is latched on the catch 64 on the feeding connector 34 of the shaft 16.

In this first position, the second shaft 40 of the optical system 14 extends beyond the distal end 23 of the first shaft 16 of the shaft part 12 by a few centimeters, as can be seen from FIG. 5.

That is to say, the distal end 41 of the second shaft 40 is distally spaced apart from the distal end 23 of the first shaft 16.

In this first position, the instrument 10 can be inserted into the uterus via the vagina and through the cervix, and, for example, an examination of the interior of the uterus can be carried out.

As a result of the inventive embodiment, only the distally protruding section of the second shaft 40 has to be inserted for this purpose. After connecting appropriate optical waveguides and connections to the suction and irrigation tap, the interior of the uterus can be observed visually or, additionally, an irrigation fluid for irrigating or dilating the uterus can be supplied.

If there should now additionally be a surgical intervention as well, the shaft part 12 is moved distally along the second shaft 40, in a corresponding fashion to the transition from FIG. 5 to FIG. 6.

To this end, the pushbutton 66 of the catch 64 must firstly be depressed in order to release the latching of the position illustrated in FIG. 5. Subsequently, the first shaft 16 can be displaced until the catch 64 latches on the other latching lug 60 (see FIG. 1) on the outer side of the second shaft 40 of the optical system 14.

This second position corresponds to the illustration of FIG. 6.

It can be seen here that the distal end 41 of the second shaft 40 of the optical system 14 comes to rest approximately level with the distal end 23 of the first shaft 16 of the shaft part 12. It can also be seen that the distal end faces of the two shafts 16 and 40 are rounded and so this results in an atraumatic curvature, and therefore the tissue dilates more easily or can be dilated more easily. The resulting curvature can have an elliptical, oval or any other design.

Figure 7:
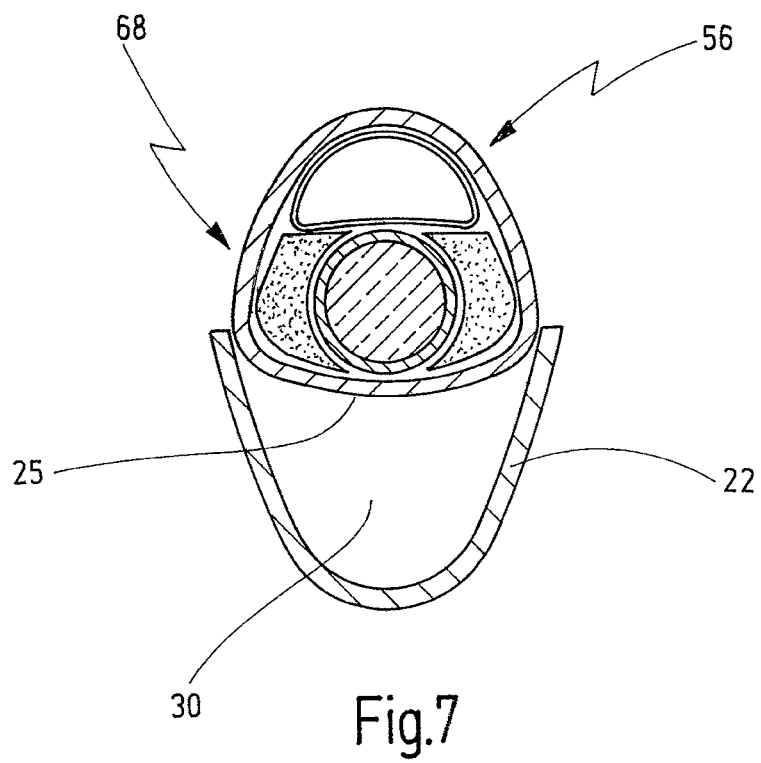
FIG. 7 shows a section along the line VII-VII in FIG. 6.
Figure 8:
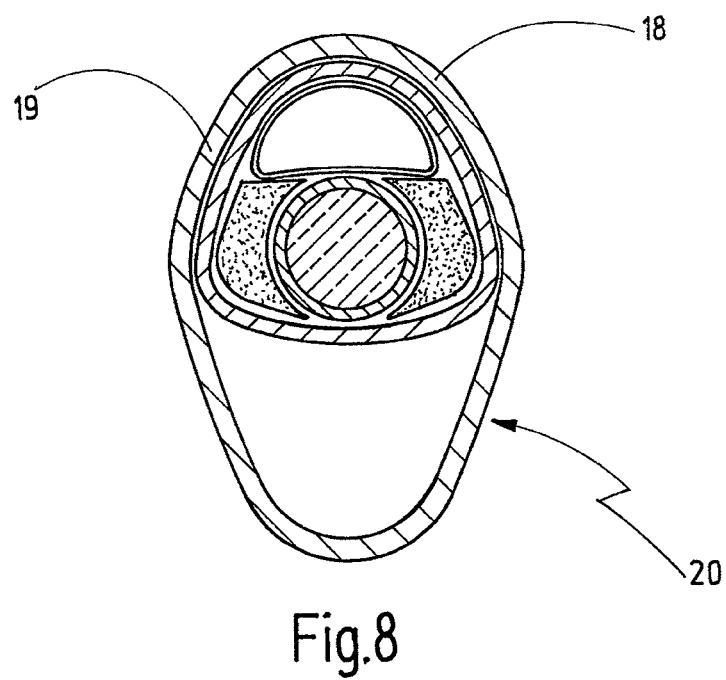
FIG. 8 shows a section along the line VIII-VIII in FIG. 6.

The sectional illustration in FIG. 7 shows that in the process, the distal shaft section 22 that is open on the side fits closely on, or is attached to, the outer cross-section profile of the cross section 56 of the second shaft 40 of the optical system 14 with its open side 25.

In this distal end region, this creates an additional instrument channel 30, which is bounded firstly by the U-shaped profile of the distal shaft section 22 and, secondly, by a lateral region of the second shaft 40 of the optical system 14.

Via the lateral connection 28, an instrument can be fed and led through the instrument channel 30, which is now created, and can be led out via the distal end 23 in order to carry out a surgical intervention in the uterus. The instrument can be retracted again after the intervention has been carried out.

Depending on how it is more expedient, or if subsequent examinations should still be carried out, the instrument 10 can then be retracted from the uterus in the assembled state illustrated in FIG. 6 or the first shaft 16 can firstly be put into the first position illustrated in FIG. 5 from the second position illustrated in FIG. 6.

It was shown until now that the distal shaft section 22 is designed as a U-shaped channel that is open on one side, but the distal shaft section 22 can also be designed as a closed channel, with it only being important that the outer profile thereof, which fits closely a circumferential section 19 on the outer side of the second shaft 40, is matched to this contour and so, overall, this results in an overall cross section 68 which leads to the rounded body by means of which both the visual observation and the surgical intervention can be carried out.

The invention claimed is:

1. A hysteroscope for insertion into a uterus, comprising: a shaft part having a first outer shaft and a second inner shaft, said first outer shaft having an approximately oval cross-sectional shape and defining a circumferentially closed channel therein, said second inner shaft being housed within said first outer shaft, said second inner shaft having an approximately triangular cross-sectional shape, said second inner shaft housing at least one channel and an optical system, said first outer shaft surrounding said second inner shaft in a first circumferential area of said approximately triangular cross-sectional shape fitting closely and matching to said first circumferential area, and surrounding said second inner shaft in a second circumferential area of said approximately triangular cross-sectional shape at a distance, thereby creating an instrument channel within said first outer shaft beside said second inner shaft, said first outer shaft and said second inner shaft being displaceable with respect to one another along said shafts, said instrument channel configured to receive instruments to carry out a surgical intervention in the uterus, wherein in a first position, said second inner shaft extends beyond a distal end of said first outer shaft, and an extending portion of said second inner shaft is configured to be inserted into a uterus without inserting said first outer shaft into the uterus, wherein in a second position said distal end of said first outer shaft comes to rest approximately at a distal end of said second inner shaft, wherein in said second position, both said first outer shaft and said second inner shaft are configured to be inserted together into the uterus, or said first outer shaft is configured to be moved over said second inner shaft already inserted into uterus; wherein a latching is provided for latching said optical system with said shaft part in said first position and in said second position, and wherein said latching, has two latching lugs separated axially from one another on said optical system and a catch on said shaft part.

2. The hysteroscope of claim 1, wherein said shaft part has a guide for guiding said second inner shaft of said optical system.

3. The hysteroscope of claim 1, wherein said optical system has a guide for guiding said first shaft of said shaft part.

4. The hysteroscope of claim 1, wherein said latching lugs are arranged on an outer side of said second inner shaft of said optical system, and said catch is arranged on a feeding connector of said shaft part.

5. The hysteroscope of claim 1, wherein said distal end of said first shaft and said distal end of said second inner shaft are rounded on a distal end face thereof.

6. The hysteroscope of claim 1, wherein said second inner shaft is provided with two strong and one soft curve.

7. The hysteroscope of claim 1, wherein the first outer shaft and the second inner shaft extend along respective longitudinal axes;
wherein the approximately oval cross-sectional shape of the first outer shaft and the approximately triangular cross-sectional shape of the second inner shaft are such that the first outer shaft and the second inner shaft are displaceable with respect to one another along the respective longitudinal axes, and such that the first outer shaft surrounds the second inner shaft in the first circumferential area of the approximately triangular cross-sectional shape in a manner that prevents the first outer shaft from rotating relative to the second inner shaft about the longitudinal axis of the first outer shaft.

8. The hysteroscope of claim 1, wherein the approximately oval cross-sectional shape of the first outer shaft and the approximately triangular cross-sectional shape of the second inner shaft are such that the first outer shaft displaceably engages the second inner shaft in the first circumferential area of the approximately triangular cross-sectional shape in a manner that prevents the first outer shaft from being rotatably displaced relative to the second inner shaft.

9. The hysteroscope of claim 1, wherein the first outer shaft is configured to guide the second inner shaft during displacement of the first outer shaft and the second inner shaft relative to one another in a direction in which the first outer shaft and the second inner shaft longitudinally extend; and
wherein the first outer shaft is tightly-fitted over the second inner shaft so as to prevent the first outer shaft and the second inner shaft from running apart in a divergent fashion during such displacement.

10. The hysteroscope of claim 1, wherein the instrument channel created within said first outer shaft has an approximately triangular cross-sectional shape.

11. A hysteroscope for insertion into a uterus, comprising: a shaft part having a first outer shaft and a second inner shaft, said first outer shaft having an approximately oval cross-sectional shape and defining a circumferentially closed channel therein, said second inner shaft being housed within said first outer shaft, said second inner shaft having an approximately triangular cross-sectional shape, said second inner shaft housing at least one channel and an optical system, said first outer shaft surrounding said second inner shaft in a first circumferential area of said cross-sectional shape of said second inner shaft fitting closely and matching to said first circumferential area, and surrounding said second inner shaft in a second circumferential area of said cross-sectional shape at a distance, thereby creating an instrument channel within said first outer shaft beside said second inner shaft, said first outer shaft and said second inner shaft being displaceable with respect to one another along said shafts, said instrument channel configured to receive instruments to carry out a surgical intervention in the uterus, wherein in a first position, said second inner shaft extends beyond a distal end of said first outer shaft, and an extending portion of said second inner shaft is configured to be inserted into a uterus without inserting said first outer shaft into the uterus, wherein in a second position said distal end of said first outer shaft comes to rest approximately at a distal end of said second inner shaft, wherein in said second position, both said first outer shaft and said second inner shaft are configured to be inserted together into a uterus, or said first outer shaft is configured to be moved over said second inner shaft when already inserted into a uterus, wherein a latching is provided for latching said optical system with said shaft part in said first position and in said second position, and wherein said latching has two latching lugs separated axially from one another on said optical system and a catch on said shaft part.

12. The hysteroscope of claim 11, wherein the instrument channel created within said first outer shaft has an approximately triangular cross-sectional shape.

* * * * *